United States Patent [19]
Zeitlin et al.

[11] Patent Number: 5,118,838
[45] Date of Patent: Jun. 2, 1992

[54] BY-PRODUCT RECOVERY WHEN OXIDIZING POLYMETHYLBENZENES TO POLYCARBOXYLIC ACIDS

[75] Inventors: Martin A. Zeitlin, Naperville; David S. Hacker, Highland Park; Kristi A. Fjare, Naperville; Diane J. Graziano, Clarendon Hills; Stacey L. Kissinger, Naperville, all of Ill.

[73] Assignee: Amoco Corporation, Chicago, Ill.

[21] Appl. No.: 722,128

[22] Filed: Jun. 27, 1991

[51] Int. Cl.⁵ .................. C07C 51/265; C07C 51/42; C07C 67/48; C07C 7/12
[52] U.S. Cl. .................................. 562/414; 560/248; 562/416; 562/417; 585/823; 585/826
[58] Field of Search .............. 562/414, 416, 417; 560/248; 585/823, 826

[56] References Cited

U.S. PATENT DOCUMENTS 2,833,816  5/1958  Saffer et al. .................. 562/416
3,089,906  5/1963  Saffer et al. .................. 562/414
4,777,287  10/1988  Zeitlin et al. ................ 562/414

Primary Examiner—Jose G. Dees
Assistant Examiner—Vera C. Clarke
Attorney, Agent, or Firm—Gunar J. Blumberg; William H. Magidson; Frank J. Sroka

[57] ABSTRACT

Substantial proportions of methyl acetate and unreacted polymethylbenzene are recovered from the waste gas produced during the oxidation of a polymethylbenzene to its corresponding polycarboxylic acid by passing the waste gas, after being cooled for removal of water vapor, through at least one bed of activated carbon and subsequently desorbing the methyl acetate and polymethylbenzene from the bed by passing a desorbing medium, such as steam, through the bed. Preferably, the cooled stream is heated to a temperature of at least 21° C. (70° F.) prior to being passed into the bed of activated carbon.

There is also disclosed an improved process for the oxidation of a polymethylbenzene to its corresponding aromatic polycarboxylic acid, which process comprises producing the polycarboxylic acid and waste gas comprising methyl acetate, water vapor, and unreacted polymethylbenzene and treating the waste gas according to the above method.

24 Claims, 2 Drawing Sheets

BY-PRODUCT RECOVERY WHEN OXIDIZING POLYMETHYLBENZENES TO POLYCARBOXYLIC ACIDS

BACKGROUND OF THE INVENTION

1. Field of the Invention

This invention relates to the removal of deleterious materials from the waste gas produced during the oxidation of polymethylbenzene to an aromatic polycarboxylic acid. More particularly, this invention relates to a method for removing by-product methyl acetate and unreacted polymethylbenzene from such waste gas.

2. Description of the Prior Art

The liquid-phase oxidation of a polymethylbenzene, such as paraxylene, to its corresponding polycarboxylic acid, i.e., terephthalic acid, is an important commercial process. A typical solvent used in this process is acetic acid. During the process, methyl acetate is produced as a by-product, the result of oxidative degradation of the acetic acid solvent. Methyl acetate is volatile and is lost usually from the process through waste gas vents.

The recovery of methyl acetate, a useful material, is desirable. It can be converted into acetic acid and methanol by hydrolysis to furnish additional acetic acid solvent. Methyl acetate can also be marketed as a fine chemical. It is a fast-evaporating solvent, is used in lacquers, in paint and varnish removers, in the perfume industry, in the manufacture of dyestuffs, and in the manufacture of cellulosic adhesives.

Methyl acetate is present in the waste gas streams produced by the liquid-phase oxidation processes for making polycarboxylic acids in very low concentrations. Consequently, the recovery of this methyl acetate is rather difficult. Recovery methods involving condensation, scrubbing, or distillation require excessive amounts of energy and/or equipment to be made efficient.

It is known that methyl acetate can be adsorbed on activated carbon and can be desorbed from the carbon. Hori et al., J. UOEH, 9(1):9-18 (1987), estimated the breakthrough time on activated carbon for multicomponent organic solvent vapors, one solvent of which was methyl acetate. Sanchez et al., INDUST. ENG. CHEM. RES., 1987, 26(9), 1880-1887, disclosed a method for adsorbing carboxylic acids on carbon and esterifying the adsorbed acids, followed by desorbing the esters. Subbotin et al., KHIM. PROM-ST., (9), 661-662 (1974), studied the dynamics of adsorbing vapor-air mixtures containing methanol and methyl acetate on activated carbon. In Japanese patent application 35194, laid open to public inspection Mar. 15, 1979, there is disclosed the adsorption of methyl acetate, as well as other ester solvents, on active carbon and the effect of repeated regeneration and repeated adsorption on the active carbon. The breakdown time is shortened after repeated adsorption of ester solvent and steam regeneration. In Japanese patent application 6924, laid open to public inspection on Jan. 14, 1984, there is disclosed a process for the recovery of organic solvents, such as methyl acetate, which process involves adsorption of the solvent, irradiating the adsorption agent, which can be active carbon, with electromagnetic microwaves after excluding the air in the chamber, withdrawing the organic solvent vapor, and cooling the adsorption agent.

Numerous patents directed to processes for the partial oxidation of polymethylbenzenes to their corresponding aromatic polycarboxylic acids. Examples of such patents are U.S. Pat. Nos. 2,833,816, 3,089,906, and 3,089,907, issued to Saffer et al., and U.S. Pat. No. 4,053,506, issued to Park et al.

None of the prior art discloses the recovery of methyl acetate, as well as unreacted polymethylbenzenes, from the waste gas streams produced during the oxidation of polymethylbenzenes to aromatic polycarboxylic acids.

Now there have been developed an improved method for the recovery of methyl acetate from the waste gas produced during the liquid-phase oxidation of a polymethylbenzene to an aromatic polycarboxylic acid and an improved process for the liquid-phase oxidation of a polymethylbenzene to an aromatic polycarboxylic acid.

SUMMARY OF THE INVENTION

According to the present invention, there is provided a method for removing methyl acetate and polymethylbenzene from the waste gas produced during the oxidation of a polymethylbenzene, such as para-xylene, to an aromatic polycarboxylic acid, such as terephthalic acid, which process comprises cooling a stream of waste gas comprising unreacted polymethylbenzene, water vapor, and methyl acetate to a temperature that is sufficient to condense a substantial portion of the water vapor to form liquid water, separating the liquid water from the stream to form a drier stream, passing the drier stream through at least one bed of activated carbon to remove substantial portions of the unreacted polymethylbenzene and the methyl acetate from the drier stream by means of adsorption of the substantial portions on said activated carbon, and subsequently passing a low-pressure steam through said at least one bed to desorb said substantial portions from said activated carbon.

In addition, there is provided an improved process for the oxidation of a polymethylbenzene to an aromatic polycarboxylic acid, wherein the oxidation is carried out in the presence of a solvent comprising acetic acid and an oxidation catalyst comprising a heavy metal catalyst and bromine. The improvement of this improved process comprises the above method for removing methyl acetate and unreacted polymethylbenzene from the waste gas produced during the process.

BRIEF DESCRIPTION OF THE DRAWINGS

The accompanying FIG. 1 provides a simplified schematic diagram of a typical process for the partial oxidation of a polymethylbenzene to its corresponding aromatic polycarboxylic acid, e.g., oxidation of para-xylene to terephthalic acid.

DESCRIPTION AND PREFERRED EMBODIMENTS

Figure 1:
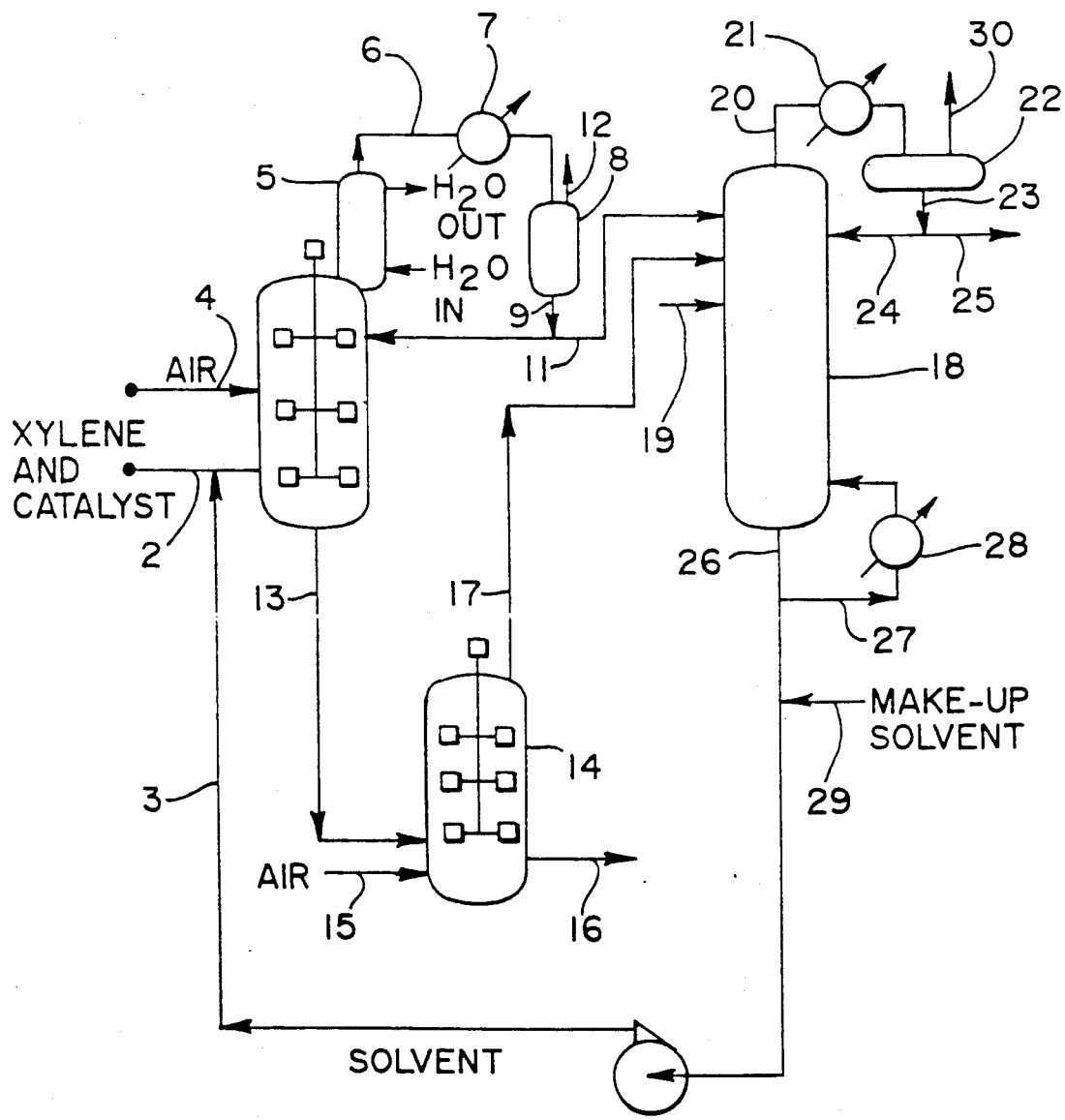

An important group of commercial processes are those processes for the partial oxidation of an alkyl aromatic with molecular oxygen. Examples of such processes are those wherein a polymethylbenzene is oxidized to its corresponding aromatic polycarboxylic acid. Typical examples of polymethylbenzenes and their corresponding aromatic polycarboxylic acids are shown hereinbelow in Table I. Such aromatic polycarboxylic acids have wide industrial applications, including the manufacture of polyesters, polyamides, fibers, and films.

TABLE I

POLYMETHYLBENZENES AND CORRESPONDING AROMATIC ACIDS

| Polymethylbenzene | Aromatic Polycarboxylic Acid |
|---|---|
| para-xylene | terephthalic acid |
| meta-xylene | isophthalic acid |
| ortho-xylene | ortho-phthalic acid |
| 1,2,4-trimethylbenzene (pseudocumene) | trimellitic acid |
| 1,2,4,5-tetramethylbenzene (durene) | pyromellitic acid |

Such oxidation is effected suitably by reacting the alky-substituted aryl compound, i.e., the polymethylbenzene, with molecular oxygen in the conjoint presence of catalytic amounts of a heavy metal catalyst and of bromine and in the presence of a monocarboxylic acid medium having from two to six carbon atoms, typically, acetic acid.

During the oxidation process, some of the acetic acid is converted to methyl acetate by-product, small amounts of which are carried out of the process by way of the waste gas and are usually lost from the process through waste gas vents. The small amounts of methyl acetate in the waste gas streams make economical recovery of methyl acetate from such streams very difficult.

The waste gas produced during the oxidation of a polymethylbenze to its corresponding aromatic polycarboxylic acid may contain only a very small amount of methyl acetate. For example, it may contain less than about 0.5 vol. % methyl acetate. Typically, the waste gas will contain methyl acetate in an amount within the range of about 0.5 vol. % to about 3 vol. %. Occasionally, the amount of methyl acetate may be somewhat higher.

The polymethylbenzene may be present in such waste gas in an amount that is much smaller than the amount for the methyl acetate. For example, the unreacted polymethylbenzene may be present in an amount that is within the range of about 100 p.p.m. (vol.) to about 2,000 p.p.m. (vol.). Occasionally, the amount may be somewhat greater.

It has now been found that the methyl acetate can be removed economically and effectively from the waste gas produced during the oxidation of a polymethylbenzene to its corresponding aromatic polycarboxylic acid by adsorbing the methyl acetate on activated carbon and desorbing subsequently the methyl acetate via the use of low-pressure steam.

The typical oxidation is effected by reacting the alkyl-substituted aryl compound, i.e., the polymethylbenzene, with molecular oxygen in the conjoint presence of catalytic amounts of a heavy metal catalyst and of bromine. The heavy metal catalyst comprises a member of the group consisting of manganese, cobalt, nickel, chromium, vanadium, molybdenum, tungsten, tin, cerium, and mixtures thereof. These metals, as well as others that have atomic numbers that are not greater than 84, are suitable for this oxidation catalyst and are presented in the "Periodic Chart of the Elements" on pages 58 and 59 of LANGE'S HANDBOOK OF CHEMISTRY, 6th edition, published by Handbook Publishers, Inc., Sandusky, Ohio, 1946. A preferred heavy metal catalyst comprises manganese and cobalt. The metal of the oxidation catalyst may be added in the elemental, combined, or ionic from. In addition, the bromine of the oxidation catalyst may be added in the elemental, combined, or ionic form. The metal or metals may be supplied in the form of metal salts of a lower aliphatic carboxylic acid, such as a metal acetate, in the form of an organic complex, such as acetylacetonate, or as metal salts, such as the borates, halides, and nitrates. Bromine may be added as ionic bromine, such as ammonium bromide or other bromine compound that is soluble in the reaction medium. Potassium bromide, tetrabromoethane, and benzyl bromide are suitable sources of bromine.

The oxidation reaction is conducted at a temperature within the range of about 150° C. (302° F.) to about 250° C. (482° F.), and preferably within the range of about 170° C. (338° F.) to about 225° C. (437° F.). It is carried out under essentially liquid-phase conditions. The temperature and pressure should be so regulated as to provide a liquid phase in the reaction zone. Generally, the pressure is maintained within the range of atmospheric to about 1,500 psig (10,444 kPa).

When the effluent from the oxidation zone is passed to an oxidation-crystallization zone, the temperature in the latter zone is maintained within the range of about 138° C. (280° F.) to about 238° C. (460° F.), preferably within the range of about 154° C. (310° F.) to about 214° C. (417° F.).

The oxidation is carried out with an oxygen-containing gas as a source of molecular oxygen. The gas may be 100% oxygen or a gas mixture containing a lower concentration of oxygen, e.g., air.

The reaction time should be sufficiently long to enable a suitable conversion to result, i.e., about 0.5 to about 25 hours or more. A reaction time within the range of about 0.5 hour to about 2 hours is preferred.

Typically, oxygen is used in an amount to provide a mole ratio of about 2 moles of oxygen per mole of substituted aromatic material to about 500 moles of oxygen per mole of substituted aromatic material; desirably, within the range of about 5 to about 300 moles of oxygen per mole of substituted aromatic material; and preferably, within the range of about 5 to about 75 moles of oxygen per mole of substituted aromatic material.

The oxidation is a liquid-phase reaction. The liquid phase may comprise all or a portion of the organic reactant, or it may comprise a reaction medium in which the organic reactant is soluble or suspended. Such reaction medium may be added to facilitate carrying out the desired reaction or recovering desired product(s). This added reaction medium is suitably a monocarboxylic acid relatively stable or inert to oxidation in the reaction system. Typically, the monocarboxylic acid contains 2 to 6 carbon atoms, e.g., acetic acid.

Suitably, the reaction medium, if a lower aliphatic monocarboxylic acid, is used in an amount to provide a ratio of about 0.1 to about 10 parts by weight reaction medium per part of aromatic material, desirably a ratio of about 0.5 to about 4, and preferably a ratio of about 1 to about 2.5 parts by weight reaction medium per part of aromatic material.

The accompanying figures and following examples will facilitate a better understanding of the process of the present invention and are presented for the purpose of illustration only. They are not intended to limit the scope of the present invention.

FIG. 1 presents a simplified schematic diagram of a typical process for the preparation of an aromatic polycarboxylic acid wherein secondary oxidation is carried out in an oxidation-crystallization zone or vessel. Since it is a simplified schematic diagram, various pieces of auxiliary equipment, such as pumps, valves, compressors, and heat exchangers, are not shown. One skilled in the art would recognize where such equipment would be needed and used. For the purpose of this illustration, the feed comprises meta-xylene.

Referring to FIG. 1, the feed and catalyst are introduced into the primary oxidation (reaction) zone 1 through line 2 after the feed and catalyst have been combined with recycled solvent from line 3. An oxygen-containing gas, such as compressed air, is introduced into reaction zone 1 via line 4. The reaction mixture is stirred or agitated continuously in reaction zone 1, which may exist in the form of one or more reactors or stages. A portion of the reaction zone-overhead condensate, which is rich in water, is removed to control effectively the water concentration in the reaction zone 1. Vapors from the reaction zone 1 pass through one or more condensers 5. A large portion of the acetic acid solvent contained in the overhead vapor is condensed and removed as liquid reflux to reaction zone 1. Uncondensed vapors pass through line 6 and heat exchanger 7. Additional vapor is condensed and the resulting condensate is collected in a secondary condenser pot 8. The condensate, which contains water-rich acetic acid, is withdrawn from condenser pot 8 through line 9 to be split into two streams, one of which is returned to reaction zone 1 via line 10 and one of which is passed to solvent recovery through line 11. Any vapor remaining in condenser pot 8 is vented through line 12.

The oxidation catalyst system employed in this process scheme is similar to the ones described hereinabove, and the process conditions utilized in this process scheme fall within the ranges of values presented hereinabove.

The polycarboxylic acid, in this case, isophthalic acid, is removed from reaction zone 1 as liquid oxidation effluent by way of line 13 and is sent to an oxidation-crystallization zone 14. A second oxygen-containing gas, e.g., compressed air, is introduced into oxidation-crystallization zone 14 via line 15. In oxidation-crystallization zone 14, a portion of the polycarboxylic acid is crystallized while additional xylene is converted to the polycarboxylic acid. The liquid effluent, a slurry containing crystals of the polycarboxylic acid, is removed from oxidation-crystallization zone 14 by way of line 16 and is passed to a second crystallizer, which is part of the product purification and recovery system (not shown). The overhead from oxidation-crystallization zone 14 is withdrawn from oxidation-crystallization zone 14 by way of line 17 and passed to first dehydration zone (solvent dehydration zone) 18.

The condensate in line 11 and solvent vapors obtained from the product purification and recovery system in line 19, along with the overhead material from the oxidation-crystallization zone 14 in line 17, are charged to first dehydration zone or tower 18 for recovery of the solvent (acetic acid). Water vapor is removed from tower 18 via line 20 through heat exchanger 21. The resulting condensate is collected in condensate drum 22. This condensate is removed from drum 22 through line 23 and is split into two streams, one of which passes through line 24 as reflux to column or tower 18 and one of which is removed in line 25 as discard.

Recovered solvent is withdrawn from column 18 through line 26. A portion of this material is passed through line 27 and reboiler 28 and reintroduced into the bottom of tower 18. Another portion of the recovered solvent in line 26 is combined with make-up solvent from line 29 and passed through line 3 to be combined with the xylene feed and catalyst in line 2. Any remaining vapor and noncondensables are vented from drum 22 via line 30.

Figure 2:
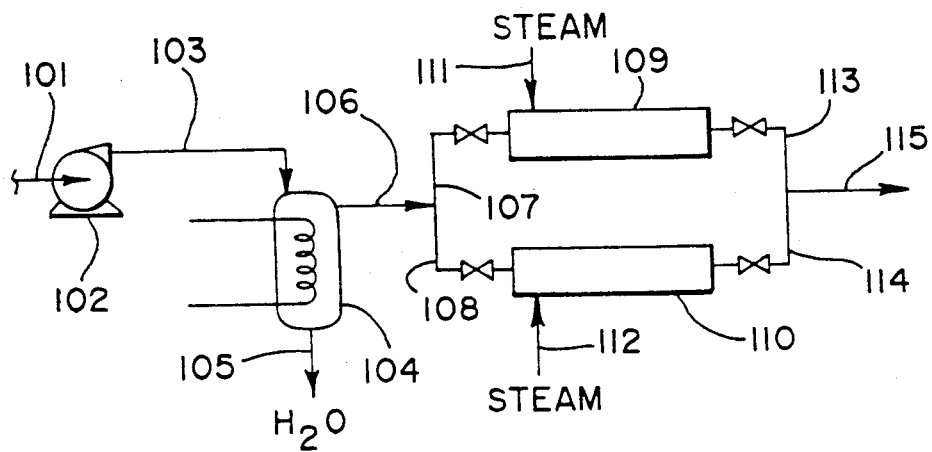
FIGS. 2 and 3 present embodiments of the method of the present invention wherein methyl acetate and unreacted polymethylbenzene are removed from the waste gas produced during the partial oxidation of a polymethylbenzene to its corresponding aromatic polycarboxylic acid.
Figure 3:
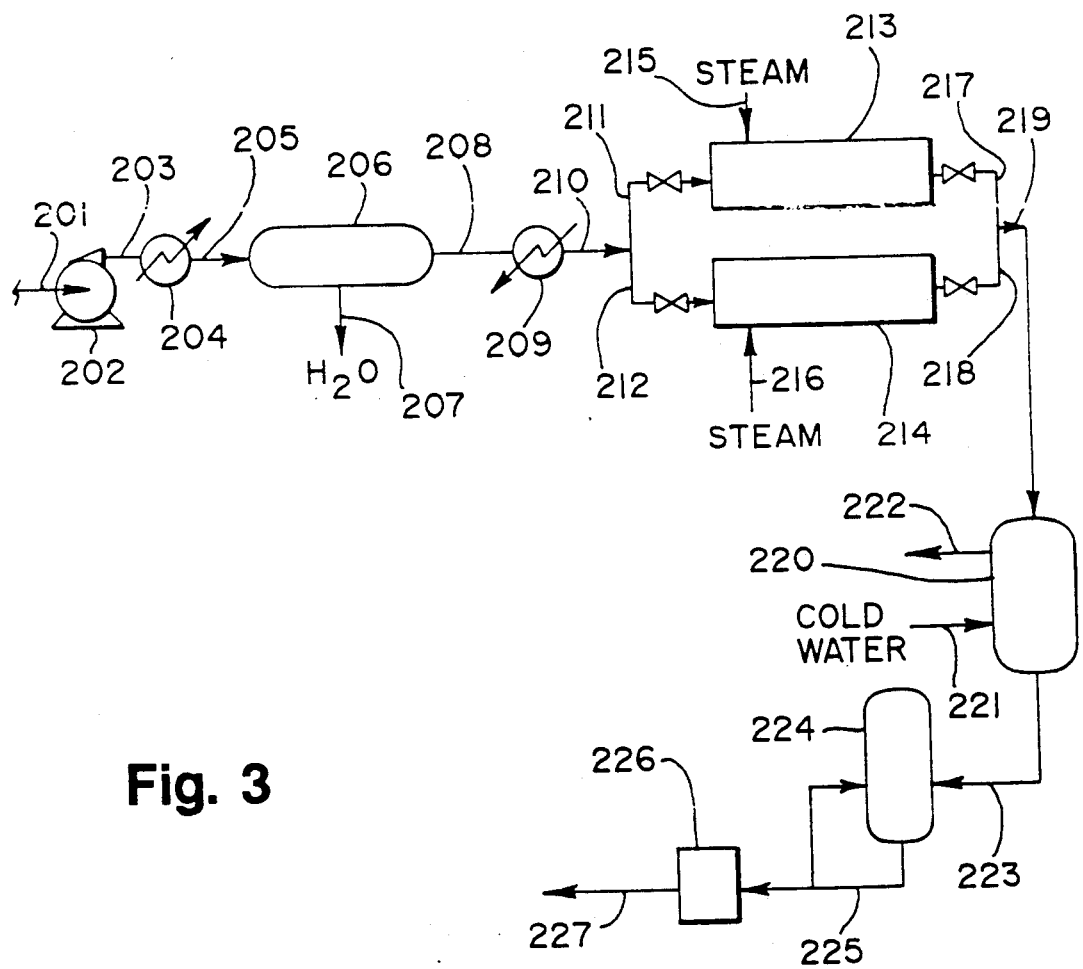

Vented waste gas from line 30 contains small concentrations of methyl acetate and unreacted polymethylbenzene, and this is a stream that can be treated by the following systems as depicted in FIGS. 2 and 3.

FIG. 2 represents a simplified schematic diagram of one embodiment of the method of the present invention wherein methyl acetate and unreacted polymethylbenzene, present in small concentrations, are removed from a waste gas produced by a process for the oxidation of the polymethylbenzene to its corresponding aromatic polycarboxylic acid.

Referring to FIG. 2, a waste gas stream from a process for oxidizing a polymethylbenzene to its corresponding polycarboxylic acid, e.g., the waste gas stream emitted from vent line 30 in FIG. 1, is passed through line 101, blower 102, and line 103 into partial condenser 104, where a substantial proportion of the water vapor in the gas is condensed from the gas and the resulting liquid water is removed from the vessel through line 105. The drier gas stream is passed from partial condenser 104 via line 106 through either line 107 or line 108 to either adsorption vessel 109 or adsorption vessel 110. Adsorption vessels 109 and 110 contain beds of activated carbon particulates and are connected by appropriate valves (not numbered) in order that one vessel can be used for adsorption while the activated carbon in the other vessel is being subjected to desorption by means of a low-pressure steam treatment. The steam is introduced into vessels 109 and 110 by lines 111 and 112, respectively, and the effluent is withdrawn from vessels 109 and 110 via lines 113 and 114, respectively, and passed through line 115 to storage or further treatment.

FIG. 3 presents a simplified schematic diagram of a second embodiment of the method for recovering methyl acetate and unreacted polymethylbenzenes from waste gas.

Referring to FIG. 3, a waste gas stream from a process for oxidizing a polymethylbenzene to its corresponding polycarboxylic acid is passed through line 201, blower 202, and line 203 to heat exchanger 204, where it is cooled sufficiently to permit a substantial portion of the water vapor in the stream to condense. The cooled stream is passed through line 205 to condensate drum 206, where the liquid water is separated from the stream, collected in the bottom of drum 206, and is withdrawn from drum 206 via line 207. The drier waste gas stream is withdrawn from drum 206 via line 208 and is passed through line 208 to heat exchanger 209, where it is heated to reduce its relative humidity. The heated stream is passed from heat exchanger 209 through line 210 into and through either line 211 or line 212 to either adsorption vessel 213 or adsorption vessel 214. The adsorption vessels 213 and 214 contain beds of activated carbon particulates and are connected by appropriate valves (not numbered) in order that one vessel can be used for adsorption while the activated carbon in the other vessel is being desorbed by means of steam or other medium. The steam or other medium is introduced into vessels 213 and 214 by lines 215 and 216, respectively, and the effluent is withdrawn from vessels 213 and 214 via lines 217 and 218, respectively, and passed through line 219 for removal from the system.

The activated carbon will remove substantial proportions of the methyl acetate and unreacted polymethylbenzenes from the waste gas. The term "substantial proportions" in this instance refers to amounts that are at least 90%. Typically, between 95% and 99% of these components are removed from the waste gas stream by the method of the present invention.

In either of the embodiments in FIGS. 2 and 3, the desorption medium is typically steam. Alternatively, hot nitrogen can be used as a desorption medium. Suitably, the nitrogen is used at a temperature within the range of about ambient temperature to about 93° C. (200° F.).

It is appropriate to cool the waste gas stream to a temperature within the range of about ambient temperature to about 21° C. (70° F.) and then reheat it to a temperature of at least 21° C. (70° F.) and a relative humidity that does not exceed 50% before it contacts the activated carbon.

Typically, the waste gas is heated to a temperature within the range of about 21° C. (70° F.) to about 74° C. (165° F.). Preferably, it is heated to a temperature within the range of about 27° C. (80° F.) to about 32° C. (90° F.).

Adsorption is conducted appropriately at a pressure within the range of about atmospheric pressure to about 515 kPa (60 psig), preferably within the range of about atmospheric pressure to about 170 kPa (10 psig).

During adsorption, the linear velocity of waste gas is suitably within the range of about 25 ft. per min. to about 90 ft. per min., preferably within the range of about 35 ft. per min. to about 50 ft. per min.

Desorption is carried out effectively at a temperature within the range of about ambient temperature to about 135° C. (275° F.) and a pressure within the range of about atmospheric pressure to about 515 kPa (60 psig). Preferably, desorption is conducted at a temperature within the range of about 132° C. (270° F.) to about 135° C. (275° F.) and a pressure within the range of about 205 kPa (15 psig) to about 308 kPa (30 psig). When steam is used as a desorption medium, it is used suitably in an amount that is within the range of about 0.3 gm. steam per gm. of carbon to about 1 gm. steam per gm. of carbon.

The sorbate is removed via line 219 to sorbate condenser 220. Cold water is introduced into condenser 220 by way of line 221 and removed therefrom via line 222. The cooled sorbate is withdrawn from condenser 220 by way of line 223 and is passed to surge drum 224. The sorbate is then passed from surge drum 224 via line 225 to a filter 226, where contaminating particles are removed therefrom. The purified sorbate comprising methyl acetate, water, and polymethylbenzene is withdrawn from filter 226 via line 227.

EXAMPLE I

A feed gas stream consisting of 2.7 vol. % methyl acetate, 0.12 vol. % para-xylene, 0.002 vol. % methanol, and 0.06 vol. % acetic acid in humid nitrogen was passed onto a bed of activated carbon containing 3800 gm. of Calgon BPL carbon. The carbon adsorption vessel had an inner diameter of three in. and a carbon bed depth of five ft. The temperature of the gas stream was 32° C. (90° F.) with a relative humidity of 50%. The linear velocity of gas across the bed was 35 ft. per min. The steam desorption was done at a pressure of 308 kPa (30 psig).

After six adsorption/desorption cycles, the working capacity of the carbon for methyl acetate to the 2% breakthrough concentration, i.e., the point when the effluent methyl acetate concentration reaches 2% of the influent methyl acetate concentration, was 18 wt. %.

Recovery of methyl acetate and para-xylene averaged 93 mole % and 78 mole %, respectively.

EXAMPLE II

In this example, the equipment, flow rates, and feed gas of Example I were used. However, the feed gas was used at a temperature of 74° C. (165° F.) with 50 relative humidity, and 3,850 gm. of Calgon BPL carbon were employed. Steam desorption was performed at a pressure of 30 psig.

After six adsorption/desorption cycles, the working capacity of the carbon to 2% breakthrough of methyl acetate was 7.7 wt. %.

Recovery of methyl acetate and para-xylene averaged 79 mole % and 99 mole %, respectively.

EXAMPLE III

Several tests were conducted to examine the effect of stream temperature and pressure on the working capacity of the carbon for adsorption of methyl acetate and methanol.

The equipment used in Examples I and II was used in this example. The carbon bed depth was five ft. The linear velocity of the feed gas during adsorption was 59 ft. per min. The feed gas contained 2.7 vol. % methyl acetate, 0.37 vol. % methanol, 0.12 vol. % para-xylene, and 0.06 vol. % acetic acid and was at a relative humidity of 50% and a temperature of 32° C. (90° F.).

Percent capacity was defined as the amount of methyl acetate adsorbed (gm. of methyl acetate per gm. carbon $\times$ 100) at the point when the effluent concentration of the sum of methyl acetate and methanol was 2% of the influent methyl acetate concentration.

The working capacity was the average of the capacities of the carbon after the capacity values had stabilized. This required a number of adsorption/desorption cycles. In each of these tests, six or more cycles were done and the results of all but the first three were averaged.

The same amount of steam was used in the experiments conducted at atmospheric pressure as in the experiments conducted at a pressure of 30 psig for a given carbon type. In Tests Nos. 3 and 4, the steam amounts were 0.45 gm. steam per gm. carbon. In Tests Nos. 5 through 8, the steam amounts were 0.55 gm. steam per gm. carbon.

Temperatures during desorption were 99° C. (210° F.) to 100° C. (212° F.) for the atmospheric pressure tests and 132° C. (270° F.) to 135° C. (275° F.) for the tests conducted at a pressure of 308 kPa (30 psig).

The results of these tests are presented hereinbelow in Table II. Please note that Calgon BPL carbon is a granular form of carbon and exists as 4$\times$8 or 4$\times$10 mesh particles, while the Westvaco and Calgon CP-IV-A carbons are pelletized. The Calgon carbons were obtained from Calgon Carbon Corp. of Pittsburgh, PA, U.S.A., and the Westvaco carbon was obtained from the Carbon Department of Westvaco Corporation of Covington, VA, U.S.A. The Westvaco carbon exists as 4×8 mesh pellets while the Calgon CP-IV-A exists as 4×6 mesh pellets.

TABLE II

| | COMPARISON OF ACTIVATED CARBONS | | | |
|---|---|---|---|---|
| Test No. | Carbon | Desorption Pressure | % Working Capacity | % Recovery |
| | | | | MeOAc[1] p-X[2] |
| 3 | Calgon BPL | 30 psig | 17 | 96  94 |
| 4 | Calgon BPL | atm.[3] | 12 | 89  83 |
| 5 | Westvaco[4] | 30 psig | 14 | 84  95 |
| 6 | Westvaco[4] | atm. | 7.5 | 91  61 |
| 7 | Calgon CP-IV-A | 30 psig | 10 | 83  90 |
| 8 | Calgon CP-IV-A | atm.[3] | 6.8 | 86  82 |

[1]MeOAc = methyl acetate
[2]p-X = para-xylene
[3]atm. = atmospheric pressure
[4]Westvaco = Westvaco NUCHAR BX-7540

The data in Table II demonstrate that for a given set of desorption conditions, either 308 kPa (30 psig) pressure or atmospheric pressure, the granular carbon had a higher adsorptive capacity for methyl acetate.

According to the present invention, there is provided a method for recovering methyl acetate and polymethylbenzene from the waste gas produced during the oxidation of a polymethylbenzene to an aromatic polycarboxylic acid, said oxidation being carried out in the presence of a solvent comprising acetic acid and an oxidation catalyst comprising a heavy metal catalyst and bromine, which method comprises cooling a stream of said waste gas comprising methyl acetate, water vapor, and unreacted polymethylbenzene to a temperature that is sufficient to condense a substantial proportion of said water vapor to form liquid water, separating said liquid water from said stream to form a drier stream, passing said drier stream through at least one bed of activated carbon to remove substantial proportions of methyl acetate and unreacted polymethylbenzene from said drier stream by means of adsorption of said substantial proportions of methyl acetate and unreacted polymethylbenzene into said activated carbon, and subsequently passing a low-pressure desorption medium through said at least one bed to desorb said substantial proportions of methyl acetate and unreacted polymethylbenzene from said activated carbon.

Substantial proportions of methyl acetate and unreacted polymethylbenzene will comprise at least 90% of either component that is present in the waste gas stream prior to treatment. Typically, about 95% to about 99% of either component will be removed from the waste gas by the method of the present invention.

A substantial proportion of the water vapor comprises at least 50% of the water vapor present in the waste gas. Typically, about 50% to about 90% will be removed by the cooling of the waste gas.

According to the present invention, there is provided also an improved process for the oxidation of polymethylbenzene to the corresponding aromatic polycarboxylic acid, which process comprises contacting at elevated temperature and pressure a feed stream comprising said polymethylbenzene in a reaction zone with an oxygen-containing gas in the presence of a monocarboxylic acid medium comprising acetic acid and an oxidation catalyst comprising conjointly a heavy metal catalyst and bromine while maintaining a liquid phase comprising said acid medium and said polymethylbenzene in said reaction zone to form products comprising said polycarboxylic acid and a waste gas comprising methyl acetate, water vapor, and unreacted polymethylbenzene, separating a stream of said waste gas from said products, recovering said polycarboxylic acid, cooling said stream to a temperature that is sufficient to condense a substantial proportion of said water vapor in said stream to form liquid water, separating said liquid water from said stream to form a drier stream, passing said drier stream through at least one bed of activated carbon to remove substantial proportions of methyl acetate and unreacted polymethylbenzene from said drier stream by means of adsorption of said substantial proportions of methyl acetate and unreacted polymethylbenzene on said activated carbon, and subsequently passing a low-pressure desorption medium through said at least one bed to desorb said substantial proportions of methyl acetate and unreacted polymethylbenzene from said activated carbon.

Therefore, in this improved process for the oxidation of a polymethylbenzene to an aromatic polycarboxylic acid, wherein said polymethylbenzene is contacted with molecular oxygen in the presence of a reaction medium comprising acetic acid and an oxidation catalyst comprising a heavy metal catalyst and bromine to form said polycarboxylic acid and a waste gas stream comprising methyl acetate, water vapor, and unreacted polymethylbenzene, the improvement which comprises cooling said waste gas stream to a temperature that is sufficient to condense a substantial proportion of said water vapor to form liquid water, separating said liquid water from said waste gas stream to form a drier stream, passing said drier stream through at least one bed of activated carbon to remove substantial proportions of methyl acetate and unreacted polymethylbenzene from said drier stream by means of adsorption of said substantial proportions of methyl acetate and unreacted polymethylbenzene on said activated carbon, and subsequently passing a desorption medium through said at least one bed to desorb said substantial proportions of methyl acetate and unreacted polymethylbenzene from said activated carbon in said at least one bed.

The method and process of the present invention are suitable for the oxidation of the polymethylbenzenes listed hereinabove to their corresponding aromatic polycarboxylic acids.

What is claimed is:

1. A method for recovering methyl acetate and polymethylbenzene from the waste gas produced during the oxidation of a polymethylbenzene to an aromatic polycarboxylic acid, said oxidation being carried out in the presence of a solvent comprising acetic acid and an oxidation catalyst comprising a heavy metal catalyst and bromine, which method comprises cooling a stream of said waste gas comprising methyl acetate, water vapor, and unreacted polymethylbenzene to a temperature that is sufficient to condense a substantial proportion of said water vapor to form liquid water, separating said liquid water from said stream to form a drier stream, passing said drier stream through at least one bed of activated carbon to remove substantial proportions of methyl acetate and unreacted polymethylbenzene from said drier stream by means of adsorption of said substantial proportions of methyl acetate and unreacted polymethylbenzene into said activated carbon, and subsequently passing a low-pressure desorption medium through said at least one bed to desorb said substantial proportions of methyl acetate and unreacted polymethylbenzene from said activated carbon.

2. The method of claim 1, wherein said drier stream is heated to a temperature within the range of about 21° C. to about 74° C. to provide a heated stream and said heated stream is then passed through said at least one bed.

3. The method of claim 1, wherein said activated carbon is present as two or more parallel beds, said drier stream is passed through at least one of said parallel beds for the removal of said substantial proportions of methyl acetate and unreacted polymethylbenzene from said drier stream by adsorption, and said desorption medium is passed through at least one of said parallel beds for the desorption of methyl acetate and polymethylbenzene from this latter bed.

4. The method of claim 1, wherein said activated carbon is present in the granular form.

5. The method of claim 1, wherein said desorption medium is steam and said steam is passed through said at least one bed to desorb said substantial proportions of methyl acetate and unreacted polymethylbenzene at a temperature within the range of about 132° C. to about 135° C. and a pressure of about 308 kPa.

6. The method of claim 2, wherein said drier stream is heated to a temperature of about 32° C. and a relative humidity that is equal to or less than 50%.

7. The method of claim 2, wherein said activated carbon is present as two or more parallel beds, said drier stream is passed through at least one of said parallel beds for the removal of said substantial proportions of methyl acetate and unreacted polymethylbenzene from said drier stream by adsorption, and said desorption medium is passed through at least one of said parallel beds for the desorption of methyl acetate and polymethylbenzene from this latter bed.

8. The method of claim 2, wherein said activated carbon is present in the granular form.

9. The method of claim 2, wherein said desorption medium is steam and said steam is passed through said at least one bed to desorb said substantial proportions of methyl acetate and unreacted polymethylbenzene at a temperature within the range of about 132° C. to about 135° C. and a pressure of about 308 kPa.

10. An improved process for the oxidation of a polymethylbenzene to the corresponding aromatic polycarboxylic acid, which process comprises contacting at elevated temperature and pressure a feed stream comprising said polymethylbenzene in a reaction zone with an oxygen-containing gas in the presence of a monocarboxylic acid medium comprising acetic acid and an oxidation catalyst comprising conjointly a heavy metal catalyst and bromine while maintaining a liquid phase comprising said acid medium and said polymethylbenzene in said reaction zone to form products comprising said polycarboxylic acid and a waste gas comprising methyl acetate, water vapor, and unreacted polymethylbenzene, separating a stream of said waste gas from said products, recovering said polycarboxylic acid, cooling said stream to a temperature that is sufficient to condense a substantial proportion of said water vapor in said stream to form liquid water, separating said liquid water from said stream to form a drier stream, passing said drier stream through at least one bed of activated carbon to remove substantial proportions of methyl acetate and unreacted polymethylbenzene from said drier stream by means of adsorption of said substantial proportions of methyl acetate and unreacted polymethylbenzene on said activated carbon, and subsequently passing a low-pressure desorption medium through said at least one bed to desorb said substantial proportions of methyl acetate and unreacted polymethylbenzene from said activated carbon.

11. The process of claim 10, wherein said drier stream is heated to a temperature of at least about 21° C. prior to being passed through said at least one bed of activated carbon.

12. The process of claim 10, wherein said activated carbon is present as two or more parallel beds, said drier stream is passed through at least one of said parallel beds for the removal of substantial proportions of methyl acetate and unreacted polymethylbenzene from said drier stream by adsorption, and said desorption medium is passed through at least one of said parallel beds for the desorption of methyl acetate and polymethylbenzene from this latter bed.

13. The process of claim 10, wherein said activated carbon is present in the granular form.

14. The process of claim 10, wherein said desorption medium is steam and said steam is passed through said at least one bed to desorb said substantial proportions of methyl acetate and unreacted polymethylbenzene at a temperature within the range of about 132° C. to about 135° C. and a pressure of about 308 kPa.

15. The process of claim 11, wherein said drier stream is heated to a temperature within the range of about 21° C. to about 74° C. prior to being passed through said at least one bed of activated carbon.

16. The process of claim 11, wherein said activated carbon is present as two or more parallel beds, said drier stream is passed through at least one of said parallel beds for the removal of substantial proportions of methyl acetate and unreacted polymethylbenzene from said drier stream by adsorption, and said desorption medium is passed through at least one of said parallel beds for the desorption of methyl acetate and polymethylbenzene from this latter bed.

17. The process of claim 11, wherein said activated carbon is present in the granular form.

18. The process of claim 11, wherein said desorption medium is steam and said steam is passed through said at least one bed to desorb said substantial proportions of methyl acetate and unreacted polymethylbenzene at a temperature within the range of about 132° C. to about 135° C. and a pressure of about 308 kPa.

19. The process of claim 15, wherein said drier stream is heated to a temperature of about 32° C. and a relative humidity that is equal to or less than 50%.

20. The process of claim 15, wherein said activated carbon is present in the granular form.

21. The process of claim 20, wherein said drier stream is heated to a temperature of about 32° C. and a relative humidity that is equal to or less than 50%.

22. In an improved process for the oxidation of a polymethylbenzene to an aromatic polycarboxylic acid, wherein said polymethylbenzene is contacted with molecular oxygen in the presence of a reaction medium comprising acetic acid and an oxidation catalyst comprising a heavy metal catalyst and bromine to form said polycarboxylic acid and a waste gas stream comprising methyl acetate, water vapor, and unreacted polymethylbenzene, the improvement which comprises cooling said waste gas stream to a temperature that is sufficient to condense a substantial proportion of said water vapor to form liquid water, separating said liquid water from said waste gas stream to form a drier stream, passing said drier stream through at least one bed of activated carbon to remove substantial proportions of methyl acetate and unreacted polymethylbenzene from said drier stream by means of adsorption of said substantial proportions of methyl acetate and unreacted polymethylbenzene on said activated carbon, and subsequently passing a desorption medium through said at least one bed to desorb said substantial proportions of methyl acetate and unreacted polymethylbenzene from said activated carbon in said at least one bed.

23. The improved process of claim 22, wherein said drier stream is heated to a temperature of at least 21° C. prior to being passed to said at least one bed of activated carbon.

24. The improved process of claim 22, wherein said drier stream is heated to a temperature of about 32° C. and a humidity that is equal to or less than 50%.

* * * * *